United States Patent
Galel et al.

[11] Patent Number: 5,498,239
[45] Date of Patent: Mar. 12, 1996

[54] CATHETER PLACEMENT BY PRESSURIZABLE TUBULAR GUIDING CORE

[75] Inventors: Zev Galel, Los Altos Hills; Yi Yang, San Francisco, both of Calif.

[73] Assignee: Guided Medical Systems, Inc., Mountain View, Calif.

[21] Appl. No.: 423,615

[22] Filed: Apr. 17, 1995

[51] Int. Cl.[6] ................................................. A61M 37/00
[52] U.S. Cl. ............................................. 604/95; 604/96
[58] Field of Search .............................. 604/95, 96, 100, 604/101, 264, 280, 283, 107, 102; 606/192–194

[56] References Cited

U.S. PATENT DOCUMENTS

| | | |
|---|---|---|
| 4,403,985 | 9/1983 | Boretos . |
| 4,475,902 | 10/1984 | Schubert . |
| 4,717,381 | 1/1988 | Papantonsakos . |
| 4,769,006 | 9/1988 | Papantonsakos . |
| 4,826,087 | 5/1989 | Chinery . |
| 5,085,635 | 2/1992 | Cragg ........................................ 604/96 |
| 5,345,937 | 9/1994 | Middleman et al. ................. 604/95 X |
| 5,352,198 | 10/1994 | Goldenberg et al. ..................... 604/95 |
| 5,376,074 | 12/1994 | Buchbinder et al. ..................... 604/96 |

*Primary Examiner*—John D. Yasko
*Attorney, Agent, or Firm*—Townsend and Townsend and Crew

[57] ABSTRACT

A catheter is provided with steering capability at its distal end by a tubular guiding member which protrudes from an opening at the distal end of the catheter and either changes shape or rotates about its longitudinal axis upon pressurization from the proximal end. In one means of actuation, the tubular member has one or more ports close to its distal end, which form laterally directed jets when the tubular member is pressurized within by fluid, the reaction force of the jets bending the tubular member in the desired direction or causing it to rotate. In another means of actuation, the tubular member either curves upon pressurization from an otherwise straight configuration upon pressurization, or straightens from an otherwise curved configuration. The tubular member can expand upon pressurization to seize the interior of the catheter body, rending both elements movable as a unit. Once the catheter is fully positioned, the tubular member can be withdrawn and replaced by functional devices or guidewires.

13 Claims, 8 Drawing Sheets

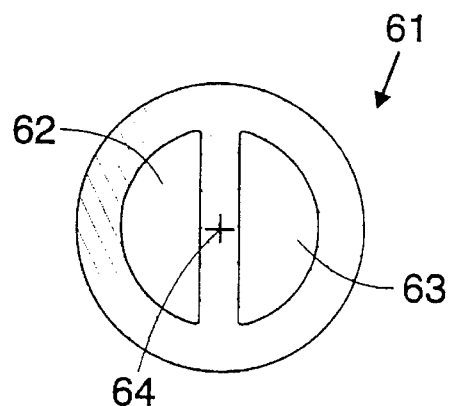
Fig. 12
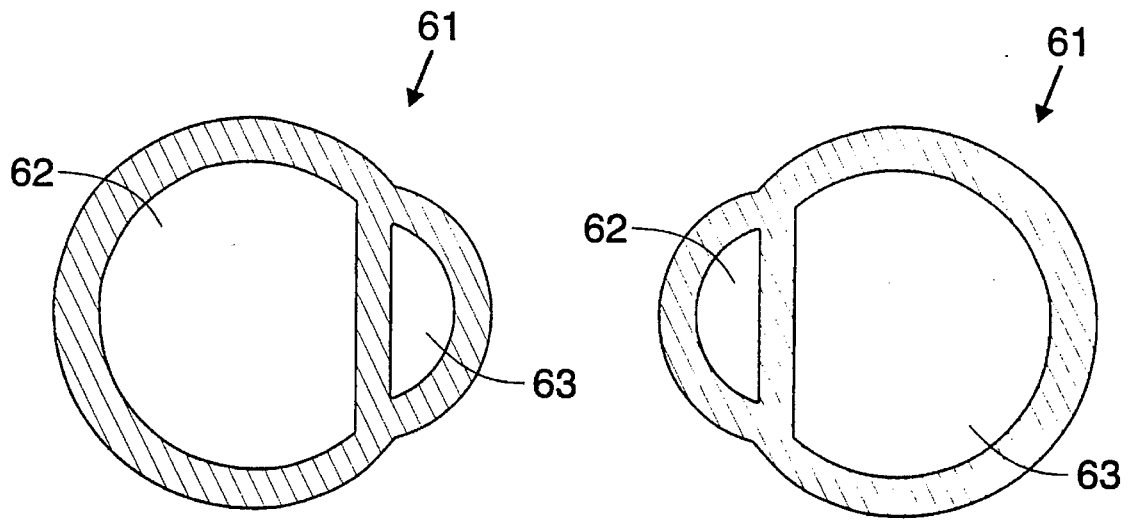
Fig. 13                    Fig. 14

CATHETER PLACEMENT BY PRESSURIZABLE TUBULAR GUIDING CORE

This invention lies in the field of medical catheters and relates to means for advancing catheters through elongated and often branched or convoluted bodily passages.

BACKGROUND OF THE INVENTION

Catheters are widely used in medical procedures, providing access to internal bodily passages and cavities for both diagnostic and therapeutic purposes without surgery. Catheter use has enabled physicians to perform sophisticated non-surgical procedures in such diverse regions of the body such as the heart and coronary arteries, the brain, and the genito-urinary tract. Catheters offer significant benefits in these procedures by lowering the cost of the procedure and reducing risks.

A critical step in catheter procedures is the insertion of the catheter into the body and the placement of the catheter tip at the appropriate location. Precise placement of the catheter tip is often critical to the function to be performed by the catheter, since the function must often be performed at a highly localized region of internal tissue without affecting adjacent areas. Placement is particularly difficult when the bodily passage is very small in diameter as well as long and tortuous, and when the interior wall of the passage is delicate and susceptible to puncture.

There are numerous examples where catheter tip placement can be critical to the success of the procedure. The removal of plaque from arteries in cardiovascular surgery is one example. Accurate steering is important in this procedure in reaching or sub-selection of the affected arteries and the location of the plaque or thrombi. In obstetrics and gynecology, directional control is important when catheters are used for the selective removal of excessive tissue and cyst growth in dilatation and curettage procedures. The same is true for the use of catheters used to deliver site-specific treatments for ovarian cancer. Directional control is also important in catheter-based urology procedures, such as the selective removal of malignant prostate tissue and the treatment of urinary tract blockages and infections. Improved biopsy methods use catheters to reduce the incidence of trauma in healthy tissue. Directional control is particularly important in neurosurgery involving the use of catheters to remove intracranial hematomas and similar procedures. Due to the high degree of tortuosity of the vasculature, sub-selection of the affected artery is difficult, requiring a long time and a high degree of dexterity by the clinician. Other procedures and applications where steering capability is important will be readily apparent to the experienced medical practitioner.

Steering mechanisms have been devised for directing the distal tip of the catheter in a desired direction by remote control from the proximal end. One such mechanism includes a series of wires running the length of the catheter body on either side of its central axis and terminating in shims or thin strips at the distal end of the catheter. The operator steers the catheter by applying tension to one shim relative to the other, thereby causing the distal end to curve in the direction of the wire to which tension has been applied. This mechanism has disadvantages, however. The wires and the mechanism at the proximal end for selectively applying tension are unwieldy and susceptible to breakage. Furthermore, the wires offer limited directional choice without twisting the entire catheter to achieve angular adjustments relative to the catheter axis.

Guidewires are widely used to assist in the placement of catheters in locations which are difficult to reach. A guidewire is typically of very narrow diameter to fit within the lumen of a catheter. This permits the operator to slide the catheter over the guidewire once the guidewire has been properly positioned. It also permits the operator to remove one catheter and replace it with another without removing the guidewire, thereby avoiding the cumbersome procedure of independently relocating the catheter tip to the region of interest. The steering of a guidewire is generally accomplished by incorporating a slight curve into the guidewire construction at its distal tip, the tip being resilient in construction to resume the curvature when relaxed. This enables the operator to direct the guidewire tip laterally into branches of the vessel. To do this, however, the operator must rotate the guidewire from the proximal end so that the curve points in the desired direction.

A further steering method described in the literature involves the use of laterally directed jets of fluid at the distal tip of the catheter, where the reaction force from the jets causes the tip to bend. A disclosure of jets of this type is found in Boretos, U.S. Pat. No. 4,403,985, issued Sep. 13, 1983. The reaction force principle is also used to advance a catheter into the bodily passage by directing the jets at an acute angle relative to the catheter axis. By simultaneously actuating two or more jets positioned at intervals around the circumference of the catheter tip, the net reaction force will be directed along the catheter axis in the distal direction. Disclosures of catheters utilizing this effect are found in Papantonakos, U.S. Pat. Nos. 4,717,381, issued Jan. 5, 1988, and U.S. Pat. No. 4,769,006, issued Sep. 6, 1988, and Schubert, U.S. Pat. No. 4,475,902, issued Oct. 9, 1984. One difficulty with these systems is that they require several independent lumens extending the length of the catheter and independent ports at the catheter's distal tip, limiting the space available at the tip for functional (therapeutic or diagnostic) elements.

These and other disadvantages of the prior art are addressed by the present invention.

SUMMARY OF THE INVENTION

The present invention resides in a steering guide for a catheter, which replaces the guidewire and provides directional steering at the distal tip upon command from the proximal end, and yet is removable from the catheter once steering of the catheter is no longer required. The steering guide is a hollow tubular member which upon pressurization from the proximal end either curves at its distal end from an otherwise straight configuration, straightens from an otherwise curved configuration, rotates around the longitudinal axis of the tubular member, or simultaneously rotates and either curves or straightens. The tubular member is of sufficiently small diameter that it fits loosely within a lumen in the catheter body, permitting an easy withdrawal of the tube, at least when the tube is not pressurized. For embodiments in which pressurization causes a change in the shape of the distal end, this is due to either a reaction force from one or more jets formed at one or more ports near the distal end or to a distortion in shape due to the pressurization alone. For embodiments in which pressurization causes the distal end to rotate, the rotation is the result of a reaction force from a jet.

The tubular member passes through a lumen running the length of the catheter body. The lumen may be the same lumen used for passage of a guidewire in over-the-wire catheters of the prior art or a lumen which has been specifically designed for the steering guide of this invention. In either case, the lumen is open at both the proximal and distal ends of the catheter so that the tubular member can be inserted at and withdrawn from the proximal end and can protrude from the distal end. In preferred embodiments, the tubular member is formed at least in part by a material of construction which is soft and elastic relative to the catheter body. In these embodiments, pressurization will cause the tubular member to expand and seize the internal wall of the catheter body lumen. In this condition, the tubular member and the catheter move as one. Deflation of the tubular member causes it to resume its relatively narrow cross section so that it fits loosely within the lumen and can be moved independently of the catheter, permitting it to be advanced into and withdrawn from the catheter. The relatively soft, elastic portion of the tubular member may be only a segment of the tubular member at its distal end, or it may constitute the full length of the tubular member.

For embodiments of the invention utilizing the reaction force of a jet, the tubular member is closed at its distal end except for one or more ports positioned a short distance from the distal end. These ports are shaped to emit jets of the pressurized fluid from the interior of the tubular member outward in lateral directions, and depending on the shape of a particular port, the reaction force can either be in a direction which intersects the axis of the tubular member or is offset from the axis. When the direction intersects the axis, the reaction force will cause the tip of the tubular member to bend or curve to one side. When the direction is offset, the jets will exert a tangential reaction force, causing rotation of the tubular member unless the rotational force is balanced by a second tangential jet.

For embodiments which do not utilize reaction forces, the tubular member is completely closed at its distal end and responds to the pressurization by a distortion in shape. Elastic tubular members which are preshaped to have a curved tip when relaxed (not pressurized) will distort to lose the curvature and straighten when pressurized. Similarly, elastic tubular members whose tips are straight when relaxed are constructed in such a manner that they distort by curving to one side when pressurized.

In each of these embodiments, the distal end of the tubular member protrudes a short distance from the distal opening of the catheter. Upon pressurization, the tubular member may lengthen elastically to protrude further.

In each of the embodiments as well, the tubular member can contain a single lumen or two or more lumens, all extending the full length of the tubular member from its proximal to its distal end. In embodiments in which jets are emitted, a single lumen may open at a single port to form a single jet. Alternatively, the single lumen may have two or more ports near the distal end to provide an added steering effect from the sum of the reaction forces generated at each port. This is useful when it is desirable to avoid high pressures at the jets. Still further, the tubular member can have two or more lumens, each leading to its own lateral port near the distal end, the ports distributed around the circumference of the tubular member. An independent supply of fluid to each lumen will actuate the jets independently. In further variations when multiple ports are present, the configurations of the ports can differ from one port to the next to point the jets at different angles to serve different purposes, thereby by affording the clinician a choice, for example, between axial rotation of the tubular member and non-rotational bending of the tip. Multiple lumens may also play a role in bending the tip for tubular members which do not form jets, and in selecting the direction in which the tip will bend.

A more detailed explanation of these embodiments, as well as additional features and advantages of the invention, are offered in the description which follows.

BRIEF DESCRIPTION OF THE DRAWINGS

FIG. 12 is a cross section of a tubular member which can be substituted for that shown in FIGS. 10 and 11.

FIG. 13 is a cross section of the tubular member of FIG. 12 with one of two lumens inflated.

FIG. 14 cross section of the tubular member of FIG. 12 with the other lumen inflated.

DETAILED DESCRIPTION OF THE INVENTION AND PREFERRED EMBODIMENTS

While the invention is broad in scope and has numerous features each of which is variable to some degree, the invention is best understood by a detailed description of certain specific examples such as those shown in the attached drawings. Throughout this specification and the appended claims, the terms "proximal"and "distal" are used in the same manner as they are by medical professionals who regularly perform catheter procedures, "proximal" denoting the end of the catheter or similar device closest to the physician when the device is in place inside the patient's body, and "distal" denoting the end furthest from the physician and furthest inside the patient's body.

FIGS. 1 through 7 show various embodiments of the invention involving jets and their reaction forces.

Figure 1:
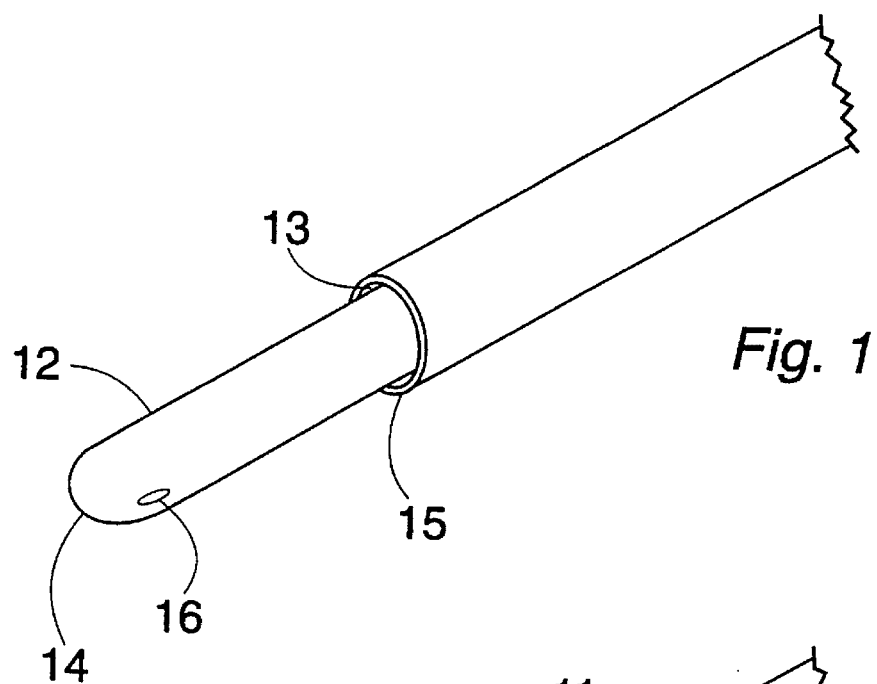
FIG. 1 is a perspective view of the distal end of a catheter and tubular guiding member representing one embodiment of the present invention.
Figure 2:
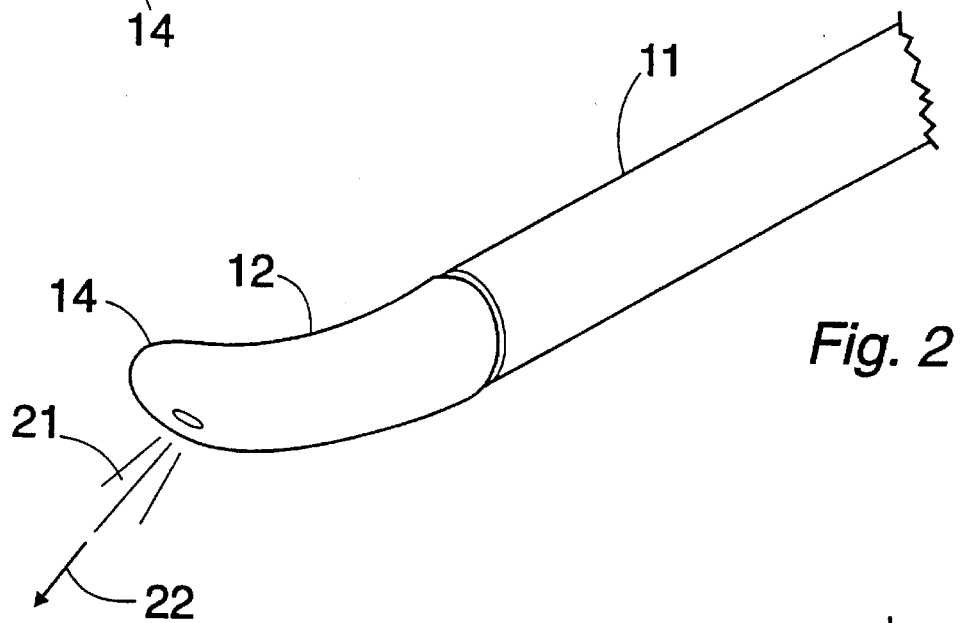
FIG. 2 is a view identical to that of FIG. 1 with the tubular guide member moderately pressurized.
Figure 3:
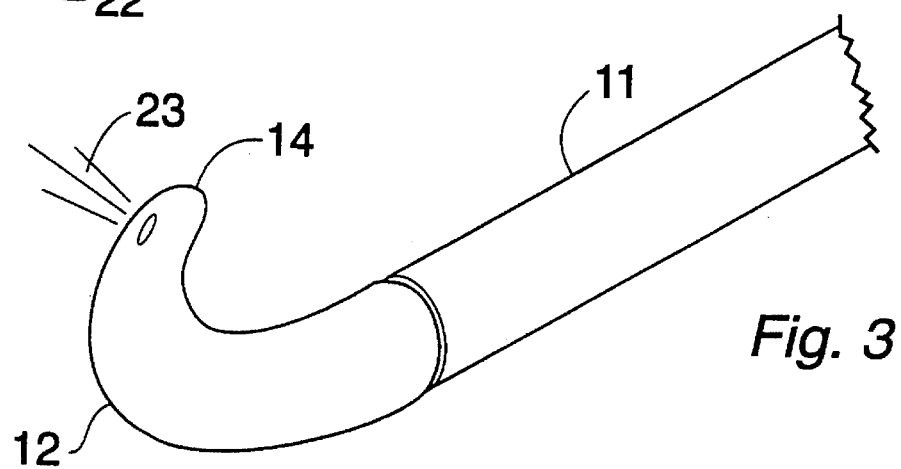
FIG. 3 is a further view identical to that of FIG. 1 with the tubular guide member pressurized to a higher degree than in FIG. 2.

FIGS. 1, 2 and 3 show the distal segment of a catheter body 11 with a tubular member 12 placed inside the catheter body. The tubular member 12 resides in a longitudinal lumen 13 in the catheter body. In the view shown in FIG. 1, the tubular member 12 is not under tension, but instead in a relaxed state, and the fit between the tubular member and the catheter body is loose enough to permit longitudinal motion of one relative to the other.

The catheter body 11 shown in FIGS. 1, 2 and 3 is a simple cylinder with a single central lumen 13. In typical implementations of this invention, the catheter body may contain one or more additional lumens, and one or more functional elements, such as diagnostic elements, imaging elements or ablative or other therapeutic elements, at the distal end. Alternatively, functional elements may be inserted in the same lumen as the tubular element after the catheter body has been fully positioned and the tubular element has been withdrawn. For convenience, these figures show only a rudimentary structure.

The distal end 14 of the tubular member protrudes beyond the distal end 15 of the catheter body by a short distance to permit bending. In preferred embodiments, this distance is about 1.0 cm or greater, more preferably about 1.5 cm to about 10.0 cm, and most preferably about 2.0 cm to about 9.0 cm. The distal end 14 of the tubular member is closed, but an opening or port 16 leading from the interior of the tubular member opens to one side of the tubular member, the port being positioned a short distance from the distal end of the tubular member. This distance may vary, but in most cases will be about 1 cm or less, and preferably about 0.5 cm or less.

Pressurization of the tubular member with a fluid in its interior causes the tubular member to assume the configurations shown in FIGS. 2 and 3. The tubular member is formed of an elastic material which readily bends under the influence of external forces and resumes its original relaxed configuration when those forces are no longer present. The port 16 in the side wall of the tubular member ejects the pressurizing fluid as a jet 21 in the direction of the arrow 22. The reaction force from the jet causes the tip of the tubular member to bend as shown in FIGS. 2 and 3.

In the absence of other external forces, the reaction force will be balanced by the resiliency of the tubular member, i.e. , its tendency to return to its relaxed state. The resiliency force increases with the degree of bend, and the tubular member bends toward an equilibrium position in which the reaction force from the jet and the resiliency force from the tubular member material are equal. The degree of bend shown in FIG. 2 is the result of a moderate pressure in the tubular member. A greater pressure produces a stronger jet 23 and thus a greater reaction force and greater degree of bend, as shown in FIG. 3.

Internal pressure in the tubular member 12 also causes the tubular member to expand and fill the catheter body lumen 13, seizing the interior wall of the lumen. When the catheter body 11 is advanced forward (in the proximal direction) in this condition, it pushes the distal tip 14 of the tubular member forward. In this manner, the tubular member is advanced into branched or tightly curved passages, with its distal tip at an appropriate angle for advancement in the desired direction.

Cross sections of various different types of tubular members designed to form jets and corresponding reaction forces are shown in FIGS. 4, 5, 6 and 7. These cross sections are perpendicular to the longitudinal axis of the tubular member and intersect the ports at which the jets are formed.

Figure 4:
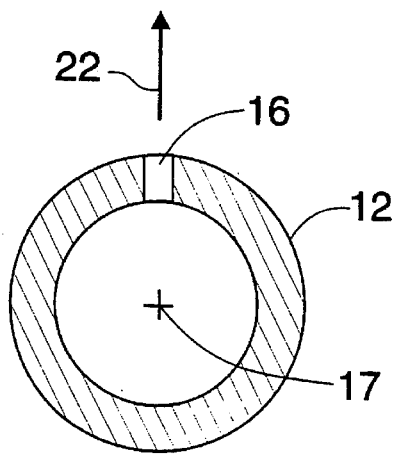
FIG. 4 is a cross section of a tubular member representing one embodiment of the invention, at a location intersecting the location of the jet.

The tubular member 12 of FIG. 4 has a single port 16, the port itself having an axis which lies radially relative to the tubular member. The direction of the jet emerging from the port is shown by the arrow 22, and the resulting reaction force intersects the axis 17 of the tubular member, causing a simple bending movement of the tubular member tip. To bend the tip in another direction, the tubular member must be rotated about its longitudinal axis by a torsional force exerted manually at the proximal end. If the tubular member is sufficiently expanded to seize the catheter body, both the tubular member and catheter body will be rotated as a unit.

Figure 5:
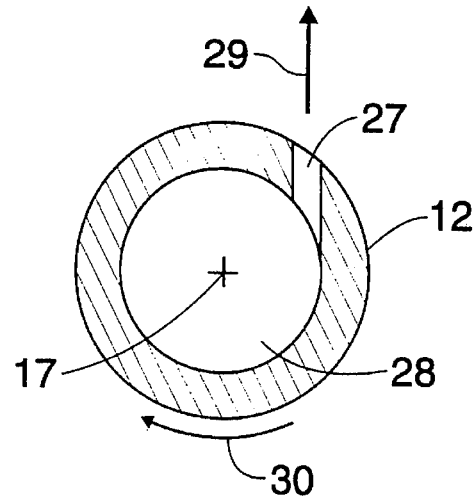
FIG. 5 is a cross section of a tubular member representing a second embodiment of the invention, at the same location.

The tubular member shown in FIG. 5 has a port 27 which is arranged with its axis tangential relative to the tubular member lumen 28, still perpendicular to but not intersecting the axis 17 of the tubular member. The emerging jet 29 is tangential as well, and the reaction force on the tubular member causes rotation of the tubular member around its longitudinal axis 17, in the direction shown by the arrow 30. Rotation can occur simultaneously with bending, since the reaction force of the jet 29 is still transverse to the longitudinal axis 17 of the tubular member. Rotation can be suppressed, however, by stabilizing the catheter body at its proximal end. Since the catheter body is seized by the tubular member under these conditions, the tubular member will likewise be prevented from rotation. The portion of the tubular member protruding from the distal end of the catheter body will then bend to one side, as its only response to the reaction force. Alternatively, the response to the reaction force can be restricted to rotation, for example by pressurizing the tubular member when the distal tip is positioned in a non-branched segment of the vasculature or other bodily passage.

Figure 6:
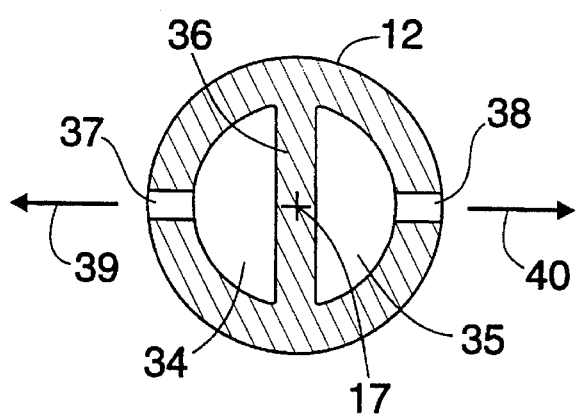
FIG. 6 is a cross section of a tubular member representing a third embodiment of the invention, at the same location.
Figure 7:
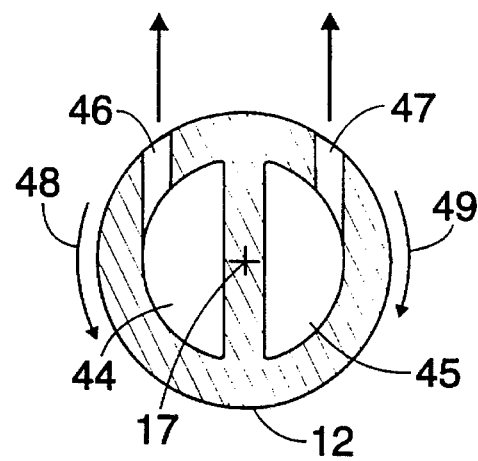
FIG. 7 is a cross section of a tubular member representing a fourth embodiment of the invention, at the same location.

The tubular members shown in FIGS. 6 and 7 differ from those of the two preceding figures by having two lumens instead of a single lumen. In FIG. 6, the two lumens 34, 35 are of equal cross section, separated by a dividing wall 36. Each lumen has a separate port 37, 38, radially oriented, forming jets in the directions indicated by the arrows 39, 40. Selective pressurization of any one lumen will produce a reaction force oposite to the direction of the jet emerging from that lumen, and the tubular member can be made to bend in either of two opposing directions.

In FIG. 7, the two lumens 44, 45 are identical to those of FIG. 6, but the ports 46, 47 are tangential. When the lumens are pressurized individually, the resulting jets produce reaction forces which cause rotation in the directions of the arrows 48, 49, respectively. The direction of rotation can thus be selected by pressurizing the appropriate lumen. When the two lumens are pressurized simultaneously and equally, the tubular member tip will bend without rotating, as a reaction force to the additive effect of the two jets, the rotating forces canceling each other. The configuration of FIG. 7 can thus be used for rotation of the tubular member in either direction or for bending of the tubular member without rotation.

The ports shown in FIGS. 4, 5, 6 and 7 are all shaped to form jets emerging in a direction perpendicular to the longitudinal axis 17 of the tubular member, whether or not the jet directions intersect the axis. Alternatively, the ports can be shaped to form jets at an angle other than perpendicular relative to the tubular member axis, provided that the jet vectors have a component perpendicular to the axis. Angles may for example range from about 60° to about 120° relative to the axis. Jets which are angled backward, i.e., in the proximal direction, can serve the added function of providing forward thrust to the tubular member in addition to steering the tubular member to one side. When two or more rearly directed ports are symmetrically distributed around the tubular member circumference, each port supplied by a separated lumen, steering may be accomplished by actuating one port to the exclusion of the others, and advancement without steering may be accomplished by actuating all ports simultaneously. With the tubular member sufficiently inflated to seize the catheter body, advancement of the catheter body is achieved as well.

FIGS. 8 through 14 show various embodiments of the invention involving shape changes achieved at the distal tip of the tubular member without reaction forces.

Figure 8:
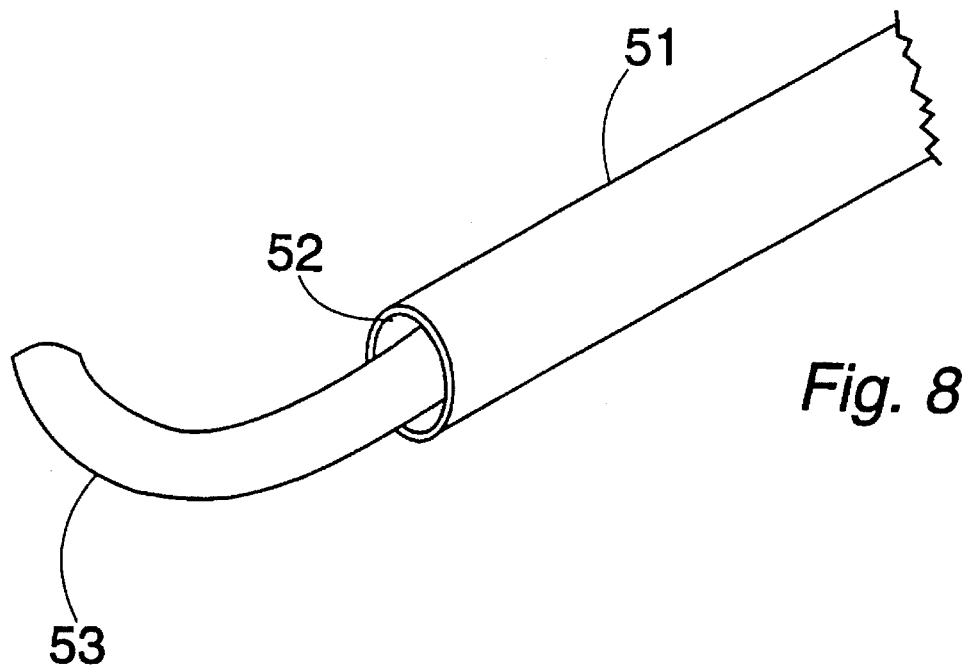
FIG. 8 is a perspective view of the distal end of a catheter and tubular guiding member representing an embodiment of the invention which does not employ jets.
Figure 9:
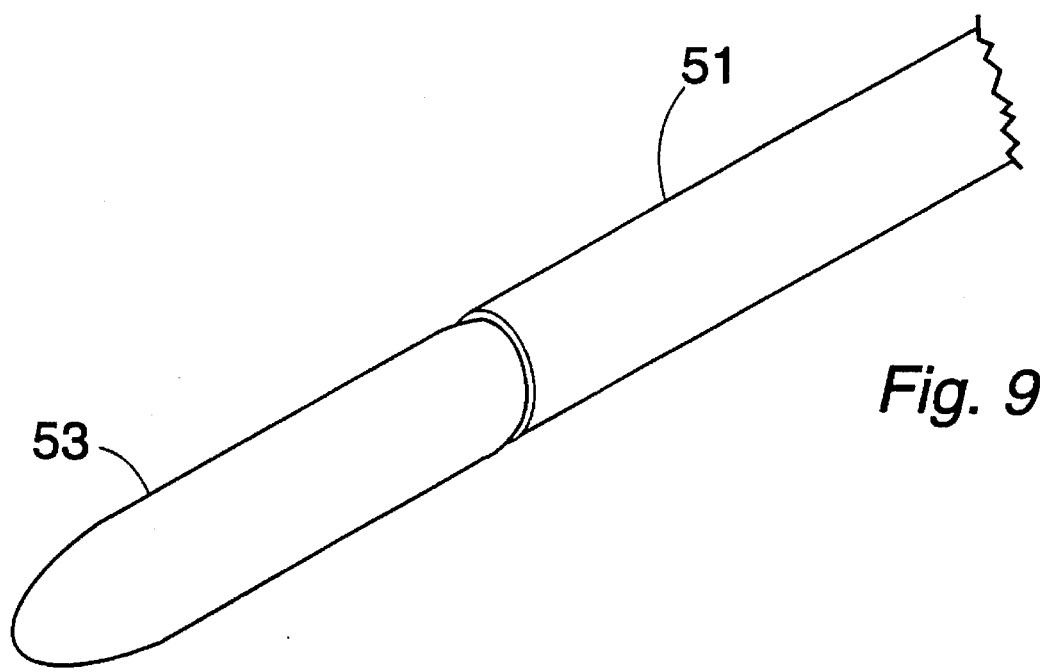
FIG. 9 is a view identical to that of FIG. 8 with the tubular guide member pressurized.

FIGS. 8 and 9 show the distal end of a catheter body 51 with a lumen 52 and a tubular member 53 passing through and protruding from the lumen, the tubular member having no distal ports. FIG. 8 shows the tubular member 53 in its relaxed, deflated condition, the tubular member loosely fitting inside the catheter body lumen 52 and having a shape memory causing its distal tip to curve as shown. FIG. 9 shows the tubular member 53 in its inflated condition, in which the tubular member has not only expanded to seize the internal wall of the catheter body lumen but has also straightened upon being made rigid by the internal pressure.

Figure 10:
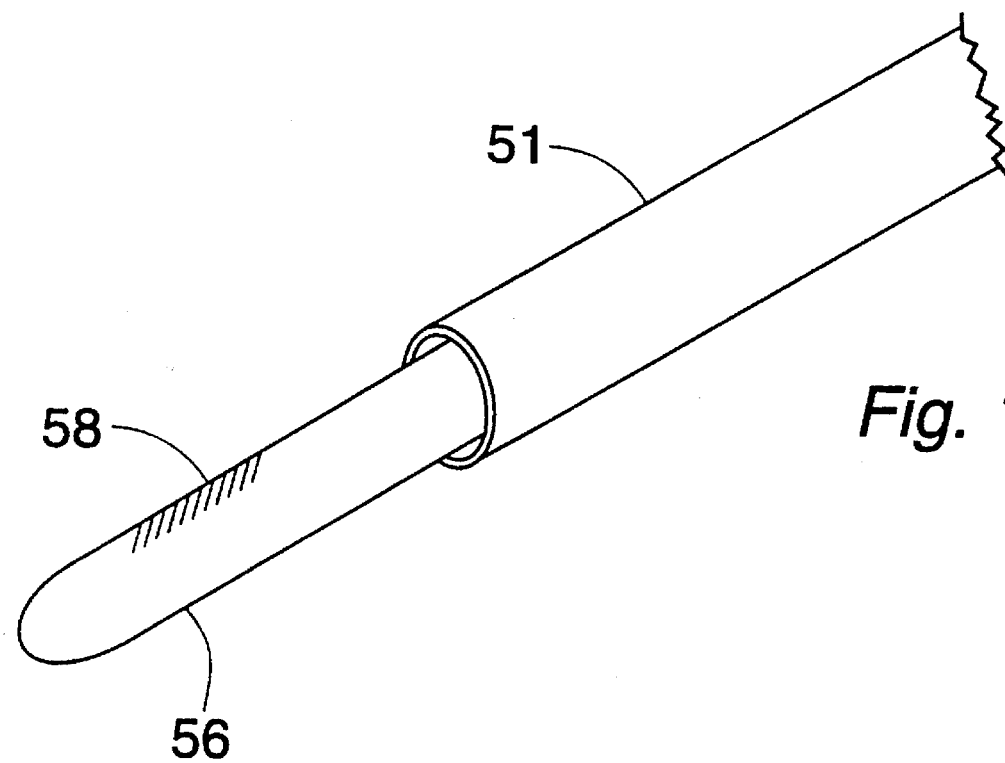
FIG. 10 is a perspective view of the distal end of a catheter and tubular guide member representing a second embodiment of the invention which does not employ jets.
Figure 11:
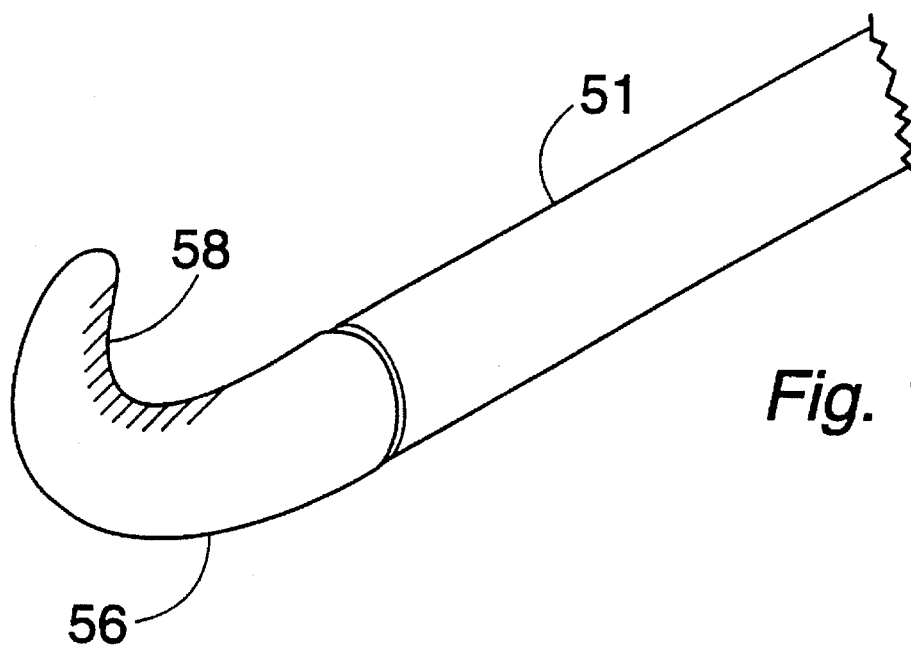
FIG. 11 is a view indentical to that of FIG. 10 with the tubular guide member pressurized.

FIGS. 10 and 11 show an embodiment which is the converse of that shown in FIGS. 8 and 9. The catheter body 51 is the same, but the tubular member 56 has no curvature when relaxed (FIG. 10), assuming its curvature only when inflated (FIG. 11).

The imposition of curvature by inflation can be achieved in a variety of ways. In the embodiment shown in FIGS. 10 and 11, one side 58 of the tubular member near the distal tip is formed of a stiffer, less expandable material than the remainder of the tubular member. Thus, when the interior of the tubular member is pressurized, the side opposing the side of low expandability will exhibit a greater expansion, resulting in the curvature shown. The formation of the stiffer, less expandable region is achievable by conventional means, for example by causing a localized higher degree of crosslinking, or by bonding a relatively non-expandable material to the region.

An alternative method of causing the curvature upon pressurization is shown in FIGS. 12 through 14, which show the tubular member in cross section. Here the tubular member 61 has two lumens 62, 63, one on either side of the longitudinal axis 64 of the tubular member, similar to the tubular members of FIGS. 4 through 7 except without ports. Pressurization of one lumen 62 exclusive of the other 63 as shown in FIG. 13 causes the tubular member to curve to the side opposite the side of the pressurized lumen. Curvature in the opposite direction is achieved by selectively pressurizing the other lumen 63, as shown in FIG. 14. In either case, only the portion of the tubular member which protrudes from the distal end of the catheter body will curve, the catheter body itself preventing the remainder of the tubular member from curving. The degree of curvature in the protruding segment can be varied by varying either the inflation pressure, the length of the tubular member protruding from the catheter, or both. The clinician can thus select the direction of curvature as well as the degree.

Figure 15:
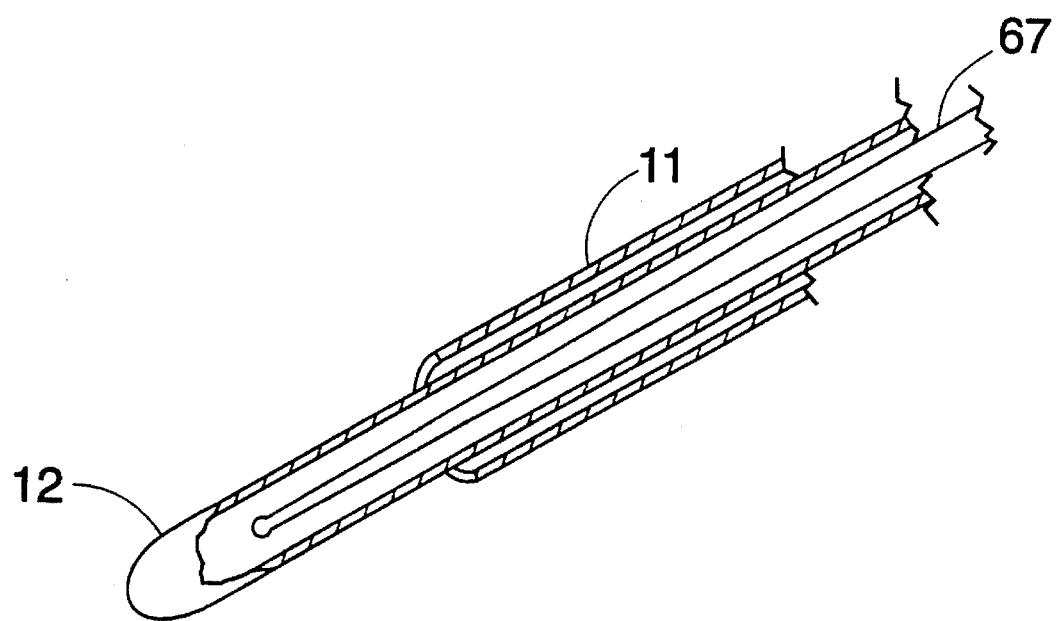
FIG. 15 is a cross section of a catheter body and tubular member containing a styler.

For each of the embodiments in FIGS. 1 through 14, additional control of both the tubular member and the catheter body can be achieved by the inclusion of a stylet inside the tubular member. FIG. 15 shows such a stylet in a cross section of the catheter body 11 and tubular member 12. The stylet is formed of a relatively rigid material such as stainless steel, but of progressively narrowing diameter in the distal direction to provide gradually increasing flexibility. The styler can be moved longitudinally relative to both the tubular member 12 and the catheter body 11 to add stiffness to the combined parts at the location where needed.

Figure 16:
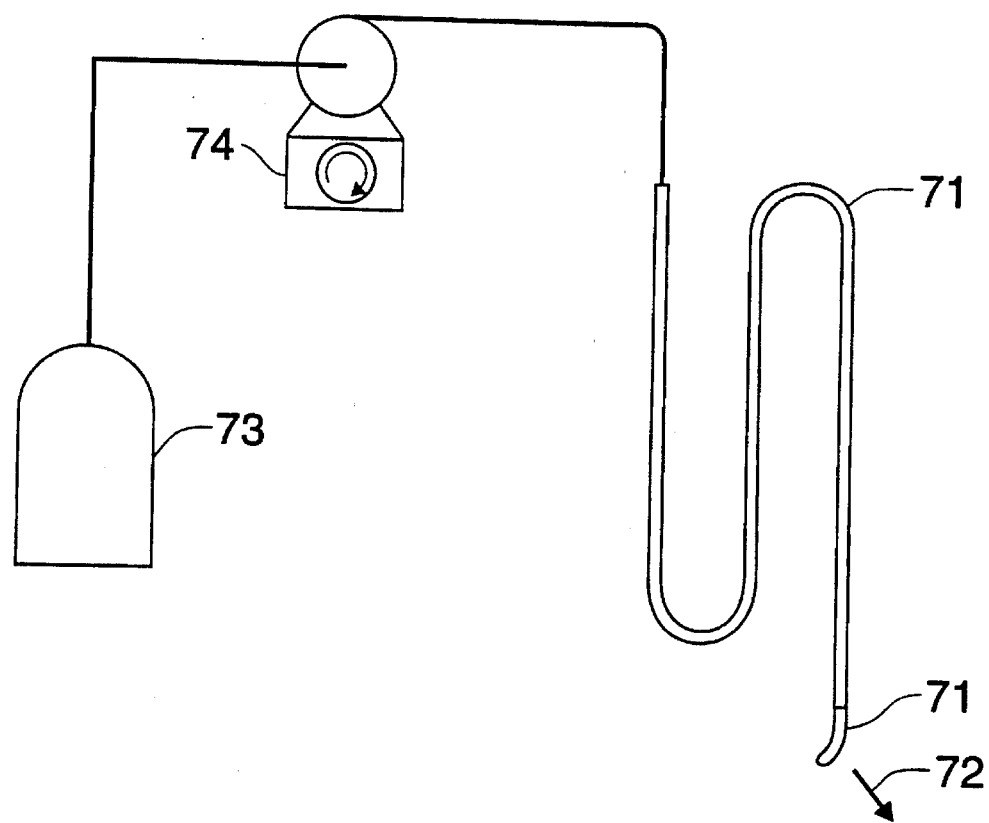
FIG. 16 is a diagram depicting the components of a single-jet catheter steering system representing one embodiment of the invention.

A complete system for catheter steering embodying the present invention is shown in FIG. 16. The catheter body 11 is shown, with the protruding distal tip 71 of the tubular member. The system shown in this figure is a jet-actuated system, using a tubular member with a single distal jet 72 to cause the tubular member to bend. Appropriate tubular members for this system are those shown in FIGS. 4 and 5. The remainder of the steering system in this embodiment consists of a fluid reservoir 73 serving as a source of fluid for the jet, and a variable speed pump 74 to feed fluid from the reservoir to the tubular member at a selected pressure depending on the angle of bend sought. The same system can be used to control the tubular member of FIGS. 10 and 11.

Figure 17:
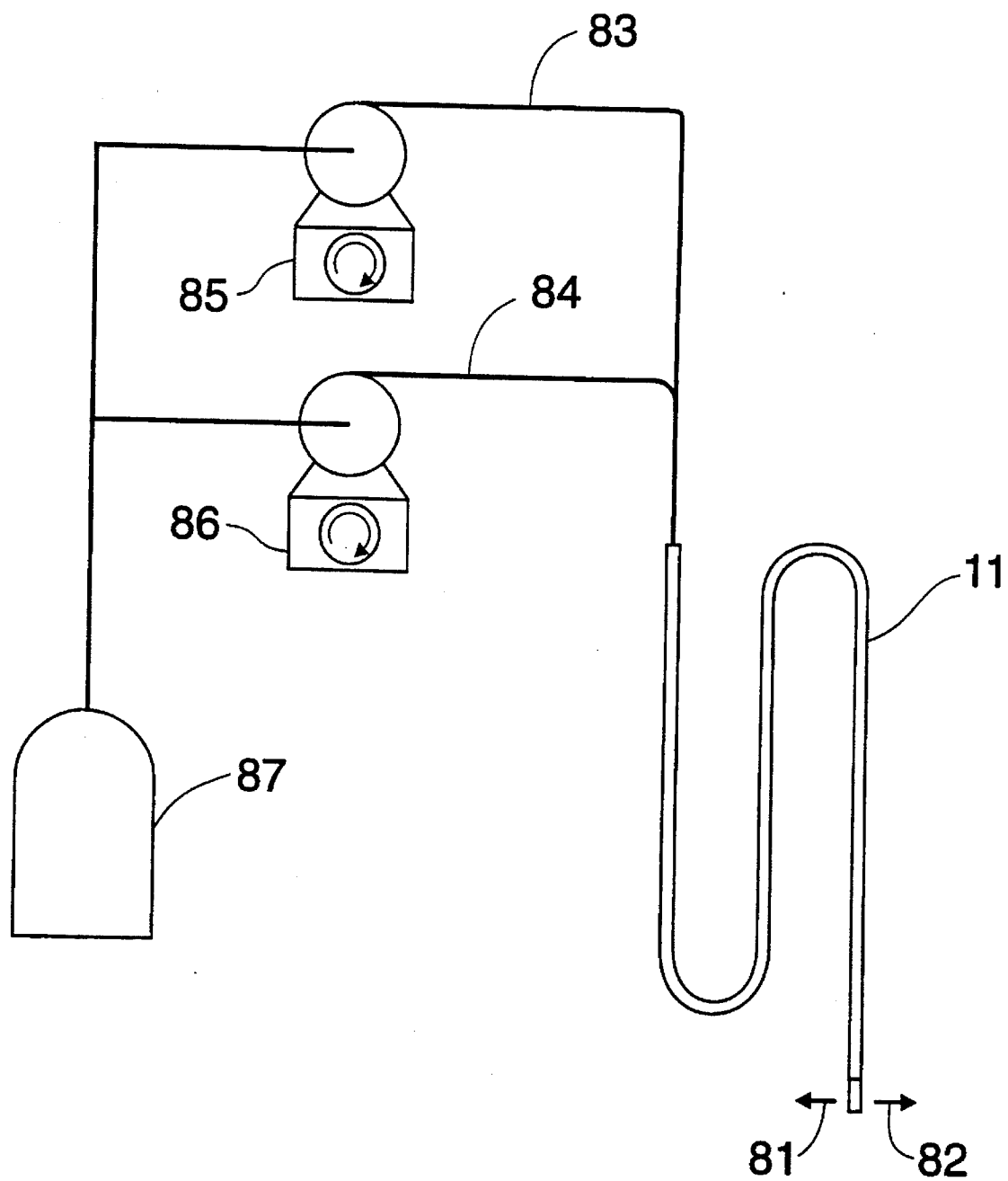
FIG. 17 is a diagram depicting the components of a dual-jet catheter steering system representing a further embodiment of the invention.

The system shown in FIG. 17 is a two-jet system, the two jets 81, 82 directed in opposite directions. An appropriate tubular member for this system is the one shown in FIG. 6, and analogously in FIGS. 12 through 14 for a tubular member without jets. The two lumens (not visible in FIG. 17) of the tubular member (corresponding to lumens 34 and 35 of FIG. 6, 44 and 45 of FIG. 7, and 62, 63 of FIGS. 12 through 14) are individually supplied by separate supply lines 83, 84, each one fed by a separate variable speed pump 85, 86, both of which draw fluid from a common reservoir 87. Valves with variable openings, single-lever valves with lever mobility in orthogonal directions rather than two individual valves, or any other conventional flow control or pressure control device may be substituted for the variable speed pumps.

Conventional components and materials may be used in the practice of this invention. The catheter body may be formed of any material conventionally used for catheters. Examples are stainless steel, polyethylene, polyvinyl chloride, polycarbonate, polyethylene terephthalate, and various polyimides. The tubular member will be of an elastic material. Examples of suitable materials are the known elastomers, including polyisoprene, polyisobutylene, polybutadiene, polychloroprene, poly(ethylene-co-propylene), poly(ethylene-co-propylene-co-diene), poly(styrene-co-butadiene), poly(isobutylene-co-isoprene), poly(styrene-co-isoprene), poly(butadiene-co-acrylonitrile), polydimethylsiloxane, silicone rubbers, polyesterurethanes and polyetherurethanes. For the pressurization fluid, physiologically compatible fluids may be used, such as water or saline.

The steering mechanism of this invention may be used in a variety of ways, depending on the needs of the particular procedure and the configuration of the passageway into which the catheter is sought to be inserted. Pressurization of the tubular member can for example be alternated with advancement of the catheter body, or both may be done simultaneously. Monitoring of the position of the catheter body can be achieved by conventional methods such as the incorporation of a radiopaque marker at or near the distal end of the catheter body, combined with fluoroscopy or other appropriate detection means. Once the catheter body is fully positioned and the tubular member is no longer needed, the tubular member can be deflated and withdrawn from the catheter body without disturbing the catheter body. Instruments can then be inserted through the catheter body, using the same lumen previously used for the tubular member.

The foregoing is offered primarily for purposes of illustration. It will be readily apparent to those skilled in the art that the components of the system, their materials of construction, their dimensions, and their configuration, arrangement and operation can be further modified or substituted in various ways without departing from the spirit and scope of the invention.

What is claimed is:

1. A combination catheter body and guiding member, said combination comprising:

a catheter body with distal and proximal ends and a catheter body lumen open at both said distal and proximal ends;

a tubular member having distal and proximal ends and a longitudinal axis and sized to be received in said catheter body lumen, said tubular member having at least one tubular member lumen and a distal segment formed of elastic material inflatable from a relaxed condition in which said tubular member fits loosely in said catheter body lumen to an inflated condition in which said tubular member seizes said catheter body, said tubular member being closed at said distal end and having at least one port within approximately 1 cm of said distal end, said at least one port shaped and arranged to eject a stream of fluid in a direction transverse to said longitudinal axis upon pressurization of said tubular member.

2. A combination in accordance with claim 1 in which said at least one port is shaped and arranged to eject a stream of fluid in a direction of from about 60° to about 120° relative to said longitudinal axis.

3. A combination in accordance with claim 1 in which said at least one port is shaped and arranged to eject a stream of fluid in a direction of about 90° relative to said longitudinal axis.

4. A combination in accordance with claim 1 in which said at least one port has an axis intersecting said longitudinal axis.

5. A combination in accordance with claim 1 in which said at least one port has an axis which does not intersect said longitudinal axis.

6. A combination in accordance with claim 1 comprising only one such port.

7. A combination in accordance with claim 1 in which said tubular member comprises two or more such tubular member lumens and such ports are equal in number to said tubular member lumens, one port communicating with each tubular member lumen.

8. A combination in accordance with claim 1 in which said tubular member comprises exactly two such tubular member lumens and exactly two such ports, one port communicating with each tubular member lumen.

9. A combination in accordance with claim 1 in which said tubular member when in said relaxed condition exceeds said catheter body in length by at least about 1.0 cm.

10. A combination in accordance with claim 1 in which said tubular member when in said relaxed condition exceeds said catheter body in length by from about 1.5 cm to about 10.0 cm.

11. A combination in accordance with claim 1 further comprising a source of pressurized fluid supplying said at least one tubular member lumen.

12. A combination in accordance with claim 11 further comprising control means for varying the pressure of said pressurized fluid supplied to said at least one tubular member.

13. A combination in accordance with claim 1 in which said tubular member comprises two or more such tubular member lumens, a plurality of ports equal in number to said tubular member lumens, one port communicating with each tubular member lumen, a source of pressurized fluid supplying said tubular member lumens, and control means for individually controlling fluid pressure supply from said source of pressurized fluid to each of said tubular member lumens.

* * * * *